United States Patent
Berggren et al.

(10) Patent No.: US 8,466,185 B2
(45) Date of Patent: Jun. 18, 2013

(54) METHODS AND ASSAYS FOR DETECTING AND TREATING HYPOGLYCEMIA

(75) Inventors: Per-Olof Berggren, Miami, FL (US); Alejandro Caicedo, Midland, FL (US); Over Cabrera, Miami, FL (US)

(73) Assignee: BioCrine AB, Solna (SE)

( * ) Notice: Subject to any disclaimer, the term of this patent is extended or adjusted under 35 U.S.C. 154(b) by 451 days.

(21) Appl. No.: 12/921,483

(22) PCT Filed: Mar. 12, 2009

(86) PCT No.: PCT/US2009/037002
§ 371 (c)(1),
(2), (4) Date: Sep. 8, 2010

(87) PCT Pub. No.: WO2009/114718
PCT Pub. Date: Sep. 17, 2009

(65) Prior Publication Data
US 2011/0021584 A1    Jan. 27, 2011

Related U.S. Application Data

(60) Provisional application No. 61/064,564, filed on Mar. 12, 2008.

(51) Int. Cl.
*A61K 31/42* (2006.01)
*A61K 31/40* (2006.01)
*C07D 207/16* (2006.01)
*C07D 261/12* (2006.01)
*C12Q 1/02* (2006.01)

(52) U.S. Cl.
USPC .......................................................... 514/380

(58) Field of Classification Search
USPC .......................................................... 514/307
See application file for complete search history.

(56) References Cited

U.S. PATENT DOCUMENTS
2007/0243177 A1    10/2007    Newgard et al.

FOREIGN PATENT DOCUMENTS
WO    02/058691    8/2002
WO    2004/060369    7/2004

OTHER PUBLICATIONS

Hayashi et al., J Secretory Granule-mediated Co-secretion of L-Glutamate and Glucagon Triggers Glutamatergic Signal Transmission in Islets of Langerhans, J Biol Chem, 278(3):1966-1974.*
Marinelli, et al., (2001) Journal of Neurophysiology 85(3):1159-1166.
Inagaki, et al. (1995) The FASEB Journal 9:686-691.
Bertrand, et al. (1993) European Journal of Pharmacology, 237(1):45-50.
Akagi, et al. (2003) J Biochem (Tokyo) 134: 353-358.
Arnt, et al. (1995) Eur J Pharmacol 285: 289-297.
Banarer, et al. (2002) Diabetes 51: 958-965.
Bertrand, et al. (1992) British Journal of Pharmacology 106: 354-359.
Bertrand, et al. (1995) The American journal of physiology 269: E551-556.
Beyreuther, et al. (2007) Eur J Clin Nutr 61: 304-313.
Cabrera, et al. (2006) Proc Natl Acad Sci USA 103: 2334-2339.
Cryer, et al. (2003) Diabetes Care 26: 1902-1912.
Franklin, et al. (2005) Diabetes 54: 1808-1815.
Fremeau, et al. (2004) Trends in Neurosciences 27: 98-103.
Gonoi, et al. (1994) Journal of Biological Chemistry 269, 16989-16992.
Gopel, et al. (2000) J Physiol 528: 509-520.
Gromada, et al. (2007) Endocr Rev 28: 84-116.
Hayashi, et al. (2003) J Histochem Cytochem 51: 1375-1390.
Hayashi, et al. (2001) J Biol Chem 276: 43400-43406.
Hayashi, et al. (2003) Diabetes 52: 2066-2074.
Hayashi, et al. (2003) J Biol Chem 278: 1966-1974.
Hollmann, et al. (1994) Annual Review of Neuroscience 17: 31-108.
Hope, et al. (2004) Diabetes 53: 1488-1495.
Ishihara, et al. (2003) Nat Cell Biol 5: 330-335.
Karlsson, et al. (1997) Am J Physiol 272: R1371-1378.
Kisanuki, et al. (1995) Diabetologia 38: 422-429.
Lees (2000) Drugs 59: 33-78.
Llorente, et al. (2006). BDTM Calcium Assay Kits and BD ACTOneTM Biosensor Technology. HotLines 10: 7-12.
Macdonald, et al. (2007) PLoS Biol 5: e 143.
MacDonald, et al. (2007) Physiology (Bethesda) 22: 113-121.
Mayer, et al. (2004) Annu Rev Physiol 66: 161-181.
Molnar, et al. (1995) FEBS Letters 371: 253-257.
Moriyama, et al. (2003) Trends Pharmacol Sci 24: 511-517.
Muroyama, et al. (2004) Diabetes 53: 1743-1753.
Olsen, et al. (2005) Endocrinology 146:4861-4870.
Ravier, et al. (2005) Diabetes 54: 1789-1797.
Rizza, et al. (1979) J Clin Invest 64:62-71.
Rorsman, et al. (1989) Nature 341: 233-236.
Saper, et al. (2003) The Journal of comparative neurology 465: 161-163.
Seeburg, (1993) Trends Pharmacol Sci 14:297-303.
Storto, et al. (2006) Molecular Pharmacology 69: 1234-1241.
Uehara, et al. (2004) Diabetes 53: 998-1006.
Unger (1985) Diabetologia 28: 574-578.
Weaver, et al. (1996) J Biol Chem 271: 12977-12984.
Wendt, et al. (2004) Diabetes 53:1038-1045.
Zhou, et al. (2004) Diabetes 53: 1482-1487.

(Continued)

*Primary Examiner* — Jeffrey S. Lundgren
*Assistant Examiner* — Zenab Olabowale
(74) *Attorney, Agent, or Firm* — McDonnell Boehnen Hulbert & Berghoff LLP

(57) ABSTRACT

Methods for regulating glucagon release and of treating hypoglycemia, and for screening drug candidates for treating hypoglycemia. The methods are useful for treating diabetes mellitus and screening drug candidates for potential efficacy.

4 Claims, 9 Drawing Sheets

OTHER PUBLICATIONS

ISR for WO 2009/114718, mailed Oct. 16, 2009.
European Search Report, EP 09 71 8671, mailed Mar. 29, 2011.

* cited by examiner

METHODS AND ASSAYS FOR DETECTING AND TREATING HYPOGLYCEMIA

STATEMENT REGARDING GOVERNMENT RIGHTS

This invention was made with U.S. Government support under Grant Nos. M01RR16587, 1R01-DK55347, 5U42RR016603, 1 R03DK075487, U24DK59635 awarded by the National Institutes of Health, Department of Health and Human Services. The U.S. Government has certain rights in this invention.

BACKGROUND

Blood glucose homeostasis is controlled by the concerted secretion of pancreatic hormones from the various cell types in the endocrine portion of the pancreas, the islets of Langerhans. The secretion of insulin and glucagon from the pancreatic β and α-cells, respectively, is regulated by nutrients as well as by autocrine, paracrine, and nervous signals. While the molecular mechanisms involved in insulin secretion are relatively well understood, those regulating glucagon secretion are not as clear. For example, researchers are currently exploring how glucagon can be so effectively released subsequent to relatively modest changes in blood glucose concentration prevailing under normal conditions.

Secretion of glucagon from α-cells is increased when the blood glucose concentration decreases (Unger, 1985; Zhou et al., 2004), but the underlying molecular mechanisms that act on the α-cell to induce glucagon release are not known. It has been proposed that high glucose levels suppress glucagon release by acting directly on α-cells (Gopel et al., 2000; Unger, 1985). Mechanistically this has been explained by the selective expression of voltage-sensitive $Na^+$ channels in α-cells that contribute to the generation of neuronal-like action potentials that are inactivated by prolonged cell membrane depolarization (Gopel et al., 2000). According to this model, the inactivation of these $Na^+$ channels suppresses α-cell activity when glucose levels are high.

Other studies, however, have shown that glucose activates α-cells by mechanisms that mirror stimulus-secretion coupling in β-cells, that is, glucose stimulates α-cells and β-cells alike (Olsen et al., 2005; Wendt et al., 2004). Therefore, inhibitory paracrine signals such as insulin, GABA, and $Zn^{2+}$ being released from the β-cell, rather than changes in the glucose concentration per se, have been suggested to be involved in the direct regulation of glucagon release (Franklin et al., 2005; Gromada et al., 2007; Ishihara et al., 2003; Kisanuki et al., 1995; Ravier and Rutter, 2005; Rorsman et al., 1989).

However, a relief of inhibitory paracrine signals does not fully explain how relatively minor decreases in glucose concentration so effectively promote glucagon release. Glutamate, a major excitatory neurotransmitter in the central nervous system, is of interest because, unlike most other signals, it may stimulate, not inhibit, glucagon secretion in the islet (Bertrand et al., 1993; Hayashi et al., 2003c). Vesicular glutamate transporters that facilitate glutamate uptake into vesicles are expressed by α-cells (Hayashi et al., 2001) and glutamate is secreted together with glucagon (Hayashi et al., 2003c).

Studies in rodent models have shown a large complexity in glutamate signaling in the islet (Moriyama and Hayashi, 2003). Results in the literature are conflicting, and to some extent the role of glutamate remains enigmatic. For instance, it has been reported that glutamate stimulates glucagon secretion via ionotropic glutamate receptors (iGluRs) (Bertrand et al., 1993), that it inhibits glucagon secretion via metabotropic glutamate receptors (mGluRs) (Uehara et al., 2004), and that it activates mGluRs and iGluRs in β-cells to increase insulin secretion (Bertrand et al., 1992; Bertrand et al., 1995; Storto et al., 2006).

The inventors have clarified the role of glutamate and developed assays and methods based on this discovery. Further, the present inventors have discovered that α-cells require positive feedback loops to produce a full glucagon response.

This application claims priority to U.S. provisional application No. 61/064,564, filed Mar. 12, 2008, which is incorporated by reference herein.

SUMMARY

The invention described herein is directed to methods and assays for detecting and regulating glucagon release and of treating hypoglycemia. In some embodiments, these methods have uses in detecting and treating diabetes.

Accordingly, it is one object to provide a method of treating hypoglycemia comprising administering an effective amount of a compound that activates an ionotropic glutamate receptor to stimulate glucagon release to a subject in need of treatment.

In one embodiment, the compound achieves this effect by activating the glutamate receptor subunit GluR6.

The ionotropic glutamate receptor may be, for example, a AMPA/kainate type receptor.

Examples of compounds expected to be effective in the method of treatment are kainate, AMPA, and (2S,4R)-4-Methylglutamic acid, (RS)-2-Amino-3-(4-chloro-3-hydroxy-5-isoxazolyl)propionic acid, 4,6-Bis(benzoylamino)-1,3-benzenedicarboxylic acid, (±)-4-(4-Aminophenyl)-1,2-dihydro-1-methyl-2-propylcarbamoyl-6,7-methylenedioxyphthalazine, 1-(4'-Aminophenyl)-3,5-dihydro-7,8-dimethoxy-4H-2,3-benzodiazepin-4-one, 1,4-Dihydro-6-(1H-imidazol-1-yl)-7-nitro-2,3-quinoxalinedione hydrochloride, GABA, Bicuculline, Insulin.

In one preferred embodiment, the compound is a glutamate analog.

The term "glutamate analog" is intended to include, for example, any compound that is sufficiently similar in structure to glutamate to bind to a glutamate receptor to exert a similar effect as glutamate.

In general, the effective dosage to be administered is expected to be about 5 mg/kg/day to about 200 mg/kg/day. However, effective dosages can be determined by those of skill in the art without undue experimentation.

In one preferred embodiment, the hypoglycemia is associated with diabetes mellitus. Thus, a method of treating Type 1 or Type 2 diabetes is provided.

Also provided is the use of a compound that activates an ionotropic glutamate receptor to stimulate glucagon release in the manufacture of a manufacture of a medicament to treat hypoglycemia.

It is also an object to provide a method of stimulating glucagon release comprising administering a compound that activates glutamate receptor subunit GluR6 of an ionotropic glutamate receptor to stimulate glucagon release. For example, the ionotropic glutamate receptor may be a AMPA/kainate type receptor. Examples of compounds expected to be useful include kainate, AMPA, GABA and insulin. In one preferred embodiment, the compound is a glutamate analog. Dosages of about 5 mg/kg/day to about 200 mg/kg/day are expected to be effective. However, effective dosages can be determined by persons of skill in the art without undue experimentation.

It is also an object to provide an assay for in vitro screening for modulators useful in treating diabetes comprising: providing islet cells in two groups, wherein the first group is a control and the second group is administered a dose of streptozotocin sufficient to destroy the β cells present; administering a test compound to both the first and second group; and measuring the potentiation of glucagon release in the first and second groups to determine the effect of the test compound, wherein a decreased in cytoplasmic calcium mobilization and/or glucagon release is indicative of a compound that is useful as a modulator. It will be appreciated by those of skill in the art that this method is useful for identifying compounds to be further tested for efficacy and safety for in vivo use.

DESCRIPTION OF THE DRAWINGS

FIG. 1(A) shows glutamate induced glucagon responses that could be blocked by CNQX (10 μM). Kainate and AMPA (both 100 μM) also elicited strong glucagon secretion. FIG. 1(B) shows quantification of results shown in FIG. 1(A) (n=5 islet preparations). FIG. 1(C) shows that the metabotropic glutamate receptor antagonist CPPG (100 μM) did not affect the glutamate-induced glucagon response. The metabotropic glutamate receptor agonists tACPD (100 μM) and ACPT-1 (100 μM) did not elicit changes in glucagon secretion. FIG. 1(D) shows the quantification of results shown in C (n=3 islet preparations). FIG. 1(E) shows insulin release was induced by high glucose (11 mM, 11G) but not by kainate (representative of 6 islet preparations). FIG. 1(F) shows glutamate elicited concentration-dependent $[Ca^{2+}]_i$ responses in human islets (n=4 islet preparations). Data were curve-fitted (Hill equation). Results in all figures are shown as mean±s.e.m.

FIG. 2(A) shows three sequential images (top) showing $[Ca^{2+}]_i$ responses to 3G, 11G, and glutamate in dispersed human islets cells (pseudocolor scale). The bottom left image shows glucagon (green) and insulin (red) immunostaining. Glucagon immunoreactive cells 2 and 3 responded to glutamate but not to 11G. Insulin immunoreactive cells 1 and 4 responded to 11G but not to glutamate. Traces of the $[Ca^{2+}]_i$ responses of these cells are shown in the bottom right. Arrows indicate the time points at which the images were taken. Bars under traces indicate stimulus application. Scale bar=50 μm. 1 mM glucose (1G), 3 mM glucose (3G), and 11 mM glucose (11G). Results are representative of 4 human islet preparations. FIG. 2(B) shows gene expression profiling of individual α-cells (left) and β-cells (right) from human (red symbols) and monkey islets (black symbols). Each row represents a single cell, each column a different glutamate receptor gene. Symbols (black or red solid circle) denote that RT-PCR products were detected.

FIG. 3(A) shows activation of iGluRs elicits inward currents in human islet cells. A representative whole-cell current evoked by kainate (100 μM) (top left panel). The amplitudes of these currents are averaged for four cells (right panel). The kainate-evoked currents could be blocked with the AMPA/kainate receptor antagonist NBQX (10 μM). Holding potential=−70 mV. Bars over current traces indicate kainate application.

FIG. 3(B) shows perifusion assays demonstrating that kainate (100 μM) stimulated large increases in glucagon secretion (responses on the left) that were abolished in the absence of extracellular $Ca^{2+}$ (0 $Ca^{2+}$+1 mM EGTA) and strongly diminished in the presence of the $Ca^{2+}$ channel blocker $La^{3+}$ (100 μM) or a combination of the specific $Ca^{2+}$ channel inhibitors nimodipine (10 μM), conotoxin GVIA (1 μM), agatoxin IVA (0.1 μM), and mibefradil (1 μM). Shown are average traces (±s.e.m., n=3 human islet preparations). The arrow indicates a switch to new solution. FIG. 3(C) shows an averaged trace (±s.e.m., n=9 cells; three monkey islet preparations) showing that $[Ca^{2+}]_i$ responses to kainate were abolished at nominal zero $Ca^{2+}$. (D) $[Ca^{2+}]_i$ responses to kainate were inhibited by CNQX (10 μM, n=7 cells), and the $Ca^{2+}$ channel blockers $La^{3+}$ (30 μM, n=14 cells) and nifedipine (10 μM, n=18 cells; Student's t-test, P<0.05). Shown are the means±s.e.m. of the peak amplitudes of the $[Ca^{2+}]_i$ responses (changes in the 340/380 fluorescence emission ratio) to kainate. Data are from three separate monkey islet preparations.

FIG. 4(A) shows confocal images of a monkey pancreatic section containing an islet. The figure also shows immunoreactivity for the vesicular glutamate transporter 1 (vGluT1) colocalized with glucagon but not insulin immunostaining. Results are representative of 3 human pancreata. FIG. 4 (B) shows representative images of islets in experiments using a fluorescent enzymatic assay to detect glutamate release. In this assay, released glutamate is a substrate in an enzymatic chain reaction that generates the fluorescent product resorufin. Resorufin fluorescence is color coded; an increase from low (blue; rest) to high (yellow; kainate) indicates increased glutamate release in response to kainate. There was little or no fluorescence increase in the absence of the enzyme glutamate oxidase (-GO; bottom panel). FIGS. 4 (C) and (D) show that in the absence of the enzyme glutamate oxidase (-GO), application of kainate and KCl did not increase resorufin fluorescence. Low glucose (1 mM, 1G; P=0.005), kainate (100 μM, kain; P<0.001), and KCl (30 mM; P<0.001) depolarization, but not high glucose (11 mM, 11G; P=0.289) induced significant glutamate release from islets as compared to kainate without GO (-GO; n=3 monkey islet preparations; one way ANOVA followed by multiple comparisons procedure, Student-Newman-Keuls method). Scale bars=20 μm in A and 50 μm in B. Arbitrary units (a.u.).

FIG. 5(A) shows an illustration of the experimental approach to measure islet glucagon secretion in real time using glucagon-sensitive biosensor cells. FIG. 5(B) shows exogenous glutamate elicited glucagon secretion from human islets as measured by $[Ca^{2+}]_i$ responses in individual glucagon biosensor cells (traces in left panel). No responses were seen in the glucagon biosensor cells in the absence of human islets (traces in right panel). FIGS. 5(C) and (D) show that lowering the glucose concentration from 6 mM to 1 mM (arrow) induced glucagon secretion as measured by $[Ca^{2+}]_i$ responses in biosensor cells (n=6 regions of interest). Rinsing caused an abrupt decrease in $[Ca^{2+}]_i$ in biosensor cells. The AMPA/kainate iGluR antagonist CNQX (10 μM) significantly inhibited the effect of glucose lowering on glucagon release by 54% (measured at 8 minutes after reducing the glucose concentration; n=3 islet preparations, Student's t-test, P=0.042).

FIG. 6(A) shows perifusion assays of mouse islets showed that glutamate (100 μM) stimulated glucagon release that was blocked by DNQX (10 μM) (left; n=6 perifusions). Kainate and AMPA (both 100 μM) also stimulated glucagon secretion (right; n=3 perifusions). FIG. 6(B) shows the metabotropic glutamate receptor agonists tACPD (100 μM) and ACPT-1 (100 μM) did not elicit changes in glucagon secretion (left). The metabotropic glutamate receptor antagonist CPPG (100 μM) did not affect the glutamate-induced glucagon response (right; n=3 perifusions). FIG. 6(C) shows that glucagon responses to glutamate (100 μM) in islets from mice lacking the metabotropic glutamate receptor mGluR4 were not different from those of islets from control mice (n=4 islet preparations per group). FIG. 6(D) shows insulin release was induced by high glucose (11 mM, 11G) but not by kainate (left), AMPA, or glutamate (right). Experiments shown are representative of 3 islet preparations.

FIG. 7(A) shows mice treated systemically with glutamate (30 mg/kg; i.p.; n=7 mice) or AMPA (15 mg/kg, n=8 mice) showed increased plasma glucagon concentrations (left; ANOVA, $P<0.05$). Plasma insulin concentrations did not change (middle). Thirty minutes after injection of AMPA, mice showed increased plasma glucose concentrations (right; solid symbols, n=8 mice, Student's t-test, $P<0.05$). Open symbols=PBS-injected mice (n=4). FIG. 7(B) shows hyperinsulinemic-hypoglycemic clamp to provide a constant hypoglycemic stimulus at ~3 mM blood glucose concentration (left) was induced with insulin infusion (middle). Glucagon secretion in response to hypoglycemia was significantly diminished in mice after NBQX infusion (10 mg/kg; red symbols, n=7) compared with saline-infused mice (black symbols; n=3; repeated measures ANOVA, $P<0.05$). Bar indicates drug infusion. FIG. 7(C) shows the glucose infusion rate needed to maintain glycemia after drug infusion was significantly larger in NBQX-treated mice (red bars; n=7) than in saline-treated mice (black bars; n=3; Student's t-test, $P<0.05$). FIG. 7(D) shows a proposed model for the regulation of glucagon secretion. Activation of α-cells depends on an initial stimulus as well as on positive feedback. When glucose levels fall, there is less suppression from β-cell-derived GABA, $Zn^{2+}$, or insulin (=initial stimulus). Positive feedback by glutamate strongly amplifies glucagon secretion. Once glucose levels increase, glucagon secretion is inhibited by insulin, $Zn^{2+}$, GABA, or a combination of the three. Without glutamate feedback, α-cells are not fully activated and glucagon secretion is deficient.

Figure 1:
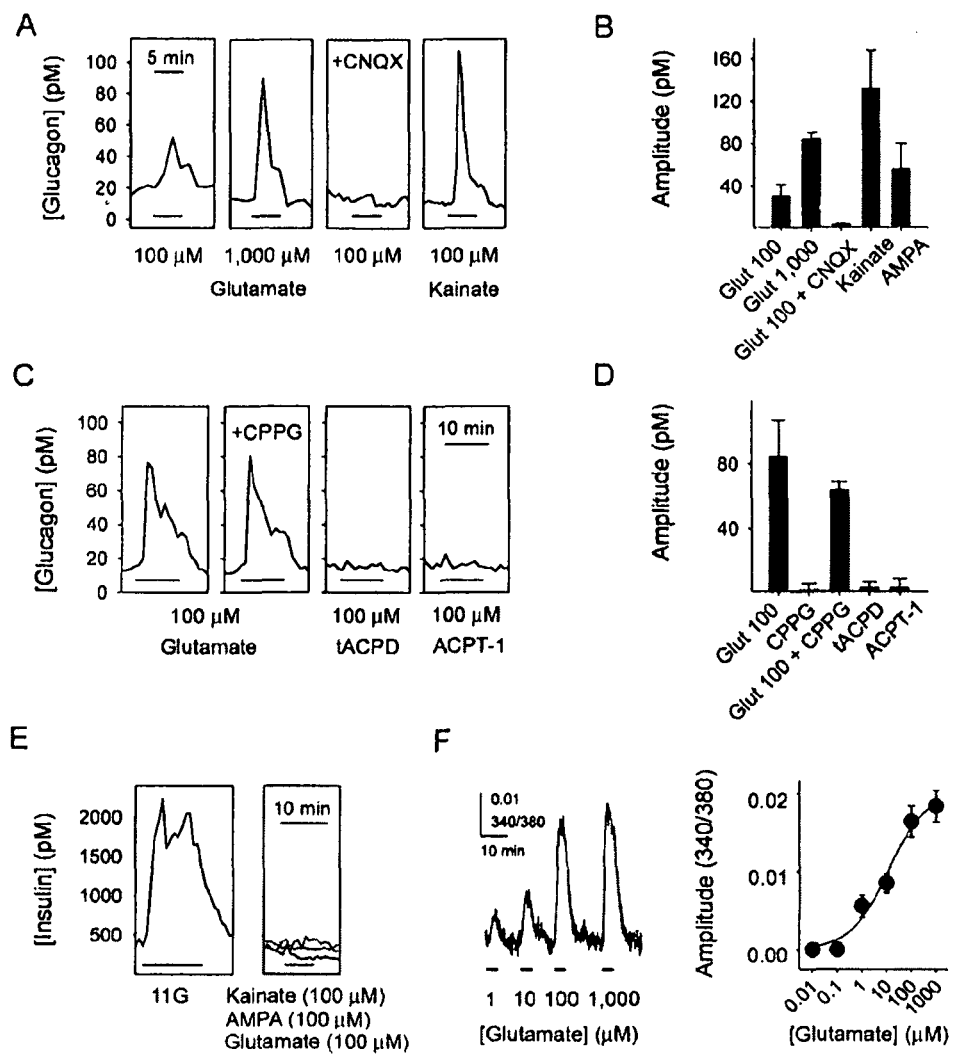
FIG. 1 A-F shows an example of activation of ionotropic glutamate receptors in human islets induces glucagon secretion.

At t=5 min, both samples were stimulated with 100 μM kainate for 5 min. The glucose was increased to 11 mM for 10 minutes and decreased again to 3 mM for the duration of the perifusion. At t=45 min, both samples (v) were stimulated with 5 mM Arginine. The amplitude of the response kainate-induced glucagon release is reduced by 55%. The amplitude of the response arginine-induced glucagon release was not statistically different. Kainate is a glutamate analog that is not metabolizable, and therefore a preferred agonist of the AMPA/Kainate receptors. Error bars represent the standards deviations for n=3 perifusions. Comparison were performed by an independent t-test.

DETAILED DESCRIPTION

Glucagon secretion from the pancreatic alpha cell is important for glucose homeostasis and to avoid life-threatening hypoglycemia. The inventors have demonstrated that glutamate is a positive autocrine signal for glucagon release. As shown herein, the inventors have also demonstrated that human and mouse alpha cells express receptors for glutamate that form membrane channels permeable for ions (ionotropic glutamate receptors). Activation of these receptors by glutamate leads to glucagon secretion. The results further showed that one of the important components of glutamate signaling in alpha cells is the glutamate receptor subunit GluR6. These investigations have shown that glutamate receptor subunit GluR6 contributes to glucose counterregulation making it a desirable pharmacological target for treating or preventing hypoglycemia.

Furthermore, the present methods are applicable to the treatment of persons with diabetes. In individuals with diabetes, glucose counterregulation is impaired. This is believed to be due to a lack of alpha cell responsiveness to changes in blood glucose, but the mechanisms remain unknown. However, as disclosed herein, in the absence of functional beta cells (as is the case in type 1 diabetes), glutamate signaling is impaired, leading to less efficient glucagon secretion.

An important feature of glucose homeostasis is an effective glucagon release from the pancreatic α-cell. The molecular mechanisms regulating glucagon secretion are still poorly understood. We now demonstrate that human α-cells express ionotropic glutamate receptors (iGluRs) that are essential for glucagon release. As a result of a lowering in glucose concentration glutamate is released from the α-cell. Glutamate then acts on iGluRs of the AMPA/kainate type, resulting in membrane depolarization, opening of voltage-gated $Ca^{2+}$ channels, increase in cytoplasmic free $Ca^{2+}$ concentration, and enhanced glucagon release. In vivo blockade of iGluRs reduces glucagon secretion and exacerbates insulin-induced hypoglycemia in mice. Hence, the glutamate autocrine feedback loop endows the α-cell with the ability to effectively potentiate its own secretory activity. This is a prerequisite to guarantee adequate glucagon release despite relatively modest changes in blood glucose concentration under physiological conditions.

The disclosed results establish glutamate as a bona fide autocrine signaling molecule in α-cells providing positive feedback for glucagon secretion in human islets. For example, it is shown that glutamate is secreted by α-cells and that α-cells, not β-cells, express iGluRs of the AMPA/kainate type. Activation of these receptors by α-cell derived glutamate generates positive feedback for α-cell function and amplifies glucagon secretion. This novel autocrine signaling pathway can explain how a modest decrease in blood glucose concentration effectively induces glucagon release from the pancreatic α-cell.

The results herein below demonstrating that glutamate provides a positive feedback for glucagon release are in agreement with studies showing that glutamate stimulates glucagon secretion (Bertrand et al., 1993), but contrast with some reports suggesting that the effect of glutamate is inhibitory and mediated by mGluR4 receptors (Moriyama and Hayashi, 2003). Glutamate was excitatory in all our physiological experiments (e.g. $[Ca^{2+}]_i$ imaging, dynamic hormone secretion assays, and in vivo plasma glucagon detection), and responses could be blocked by AMPA/kainate receptor antagonists, indicating that stimulation of glucagon release via iGluRs is the predominant effect of the glutamate autocrine feedback loop. Our findings showing that agonists and antagonists for metabotropic glutamate receptors did not affect glucagon secretion demonstrate that these receptors are not involved in glutamate signaling in human α-cells. Because glucagon responses to glutamate were not altered in mice lacking mGluR4 receptors, we further conclude that this receptor likely does not contribute to α-cell responses to glutamate as suggested previously (Uehara et al., 2004).

Islet cell immunostaining with antibodies recognizing the AMPA receptor subunits GluR2 and GluR3 was not specific, that is, it could not be blocked by peptide preadsorption of the antibody. Because of the modest effects of glutamate receptor ligands on insulin secretion and the low incidence of glutamate-responsive β-cells in previous studies, authors have cautioned to ascribe a major functional role to glutamate receptors in the regulation of insulin secretion (Molnar et al., 1995). This is in line with our single cell RT-PCR results showing that β-cells did not express iGluRs. Our findings showing that β-cell activity and insulin secretion could not be stimulated with glutamate receptor agonists further indicate that glutamate signaling and in particular iGluRs are not directly involved in the regulation of insulin secretion.

To be relevant for paracrine or autocrine signaling, glutamate has to be released from islet cells in response to physiological stimulation. Studies using rodent islets have shown that α-cells express vesicular glutamate transporters that facilitate glutamate uptake into secretory vesicles (Hayashi et al., 2001) and that glutamate is present in glucagon secretory granules and is co-released with glucagon (Hayashi et al., 2003c). In the present study we found that human and monkey α-cells express the vesicular glutamate transporter vGluT1. The inventors detected glutamate secretion in response to specific stimulation of α-cells, confirming that α-cells are a major source of glutamate in primate islets. Although neurons or nerve terminals could also release glutamate, the inventors' results were obtained using cultured isolated islets that did not contain neuronal elements (see also Karlsson et al., 1997).

Figure 5:
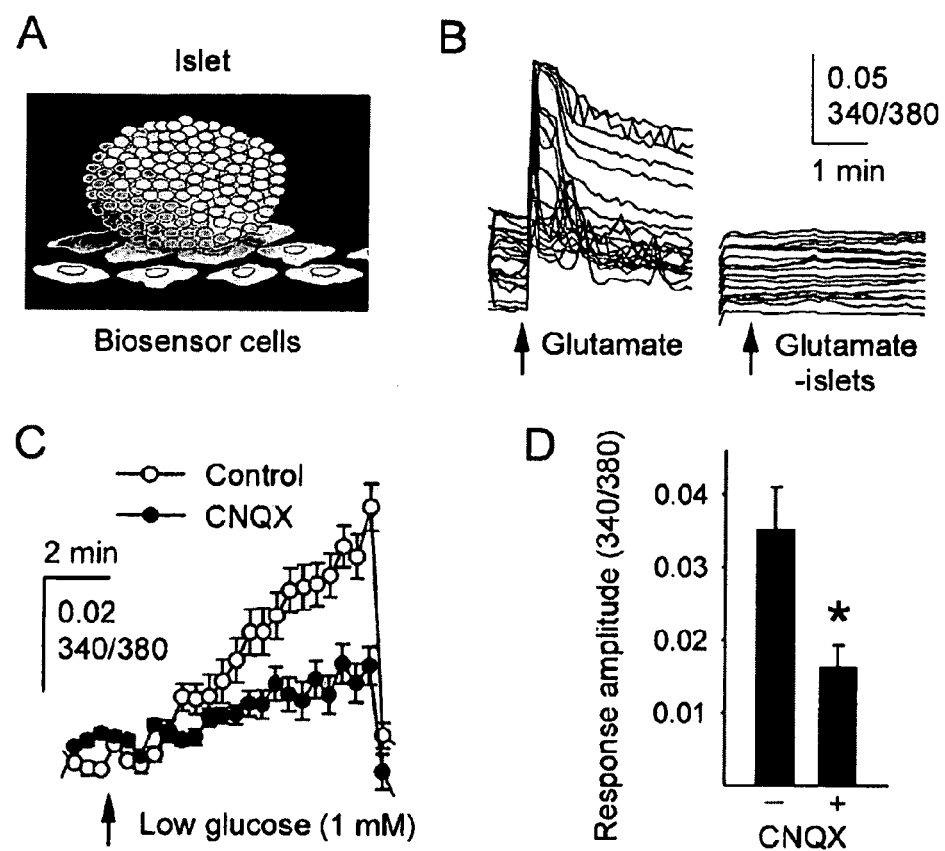
FIG. 5 shows an example of a stimulatory autocrine glutamate feedback loop being needed for effective glucagon release.

Because the inventors found that α-cells secrete glutamate and because iGluRs were exclusively expressed in α-cells, it is believed that that glutamate is an autocrine signaling molecule. Our results showing that blockade of iGluRs diminishes the glucagon response to a lowering in glucose concentration (see FIG. 5) indicate that glutamate is endogenously released and corroborate that glutamate signaling provides a positive autocrine feedback loop.

The notion of an autocrine loop with positive feedback also helps explain how α-cells respond appropriately to a lowering in the plasma glucose concentration. By using the hypoglycemic clamp in mice, we stimulated glucagon secretion in vivo and found that the glucagon response was significantly diminished by pharmacological blockade of iGluRs. In these mice hypoglycemia was exacerbated, indicating that iGluRs need to be activated for a full glucagon response in the context of glucose counterregulation. While we cannot rule out any additional effects glutamate may have on central and peripheral neurons that could indirectly affect α-cells, our in vitro data demonstrate that the α-cell is a major direct target for glutamate and that intraislet glutamate signaling can work independently of nervous input. Therefore, these results demonstrate that the glutamate autocrine feedback loop is activated in α-cells to potentiate glucagon secretion.

Figure 7:
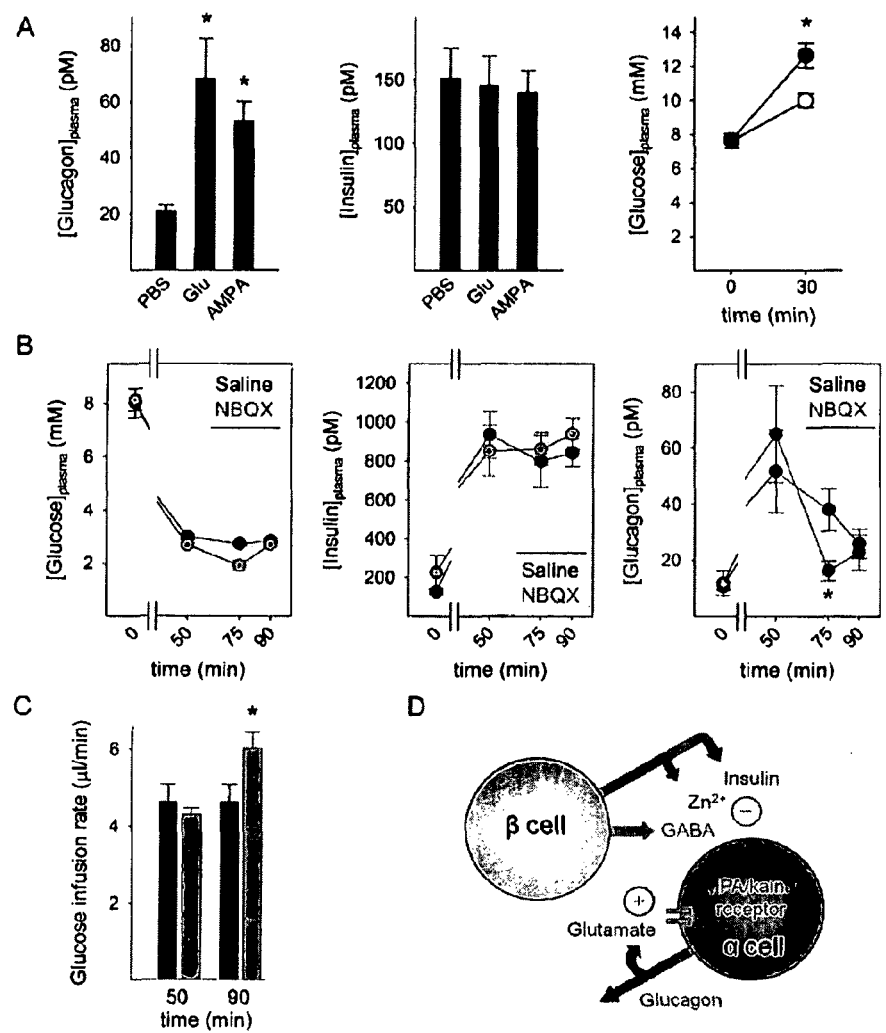
FIG. 7 A-D show an example of in vivo activation of iGluRs to stimulate glucagon secretion.
Figure 8:
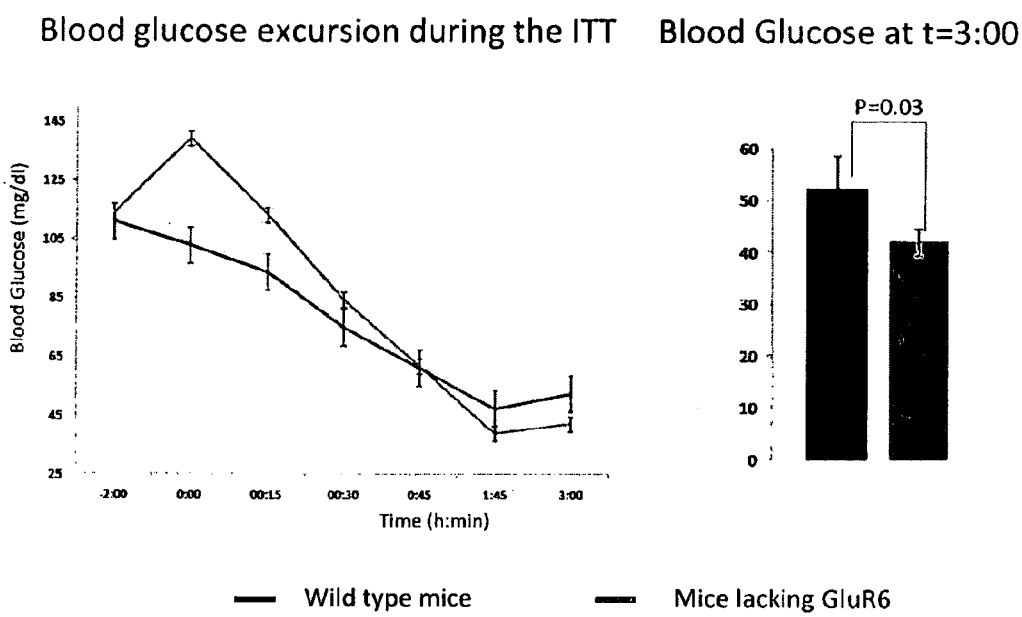
FIG. 8 shows an example of an insulin tolerance test (ITT) performed to assess glucose counter-regulation on mice lacking the subunit 6 of the AMPA/kainate receptor (GluR6). Mice in both groups were injected at t=0:00 with insulin to induce hypoglycemia. Mice lacking GluR6 progress faster and go deeper into hypoglycemia than wild type mice, indicating that the presence of this subunit is important during glucose counter-regulation. Note that from the time that mice lacking GluR6 were restrained (−2:00) to the time they were injected with insulin (0:00), there was an increase in blood glucose. This effect is likely to be independent of glucose counter-regulation since, at this level of glucose, the mechanisms of glucose counter-regulation are not operational. Notably, mice lacking GluR6 progress faster into hypoglycemia as indicated by the slope of the glucose excursion curve. After 45 minutes of the insulin administration, mice entered into a frank hypoglycemic state, and it is here where the mechanisms of glucose counter-regulation commence to act to reestablish a normal blood glucose level. In the mice lacking GluR6 and the wild type mice, blood glucose levels continue to decrease after 45 minutes, but blood glucose in wild type mice quickly recovered after 1:45, and it does so at significantly higher levels than in mice lacking GluR6 at 3 hours after the insulin administration. Error bars represent the standard error of the mean for n=8 (wild type mice) and n=10 (mice lacking GluR6).
Figure 9:
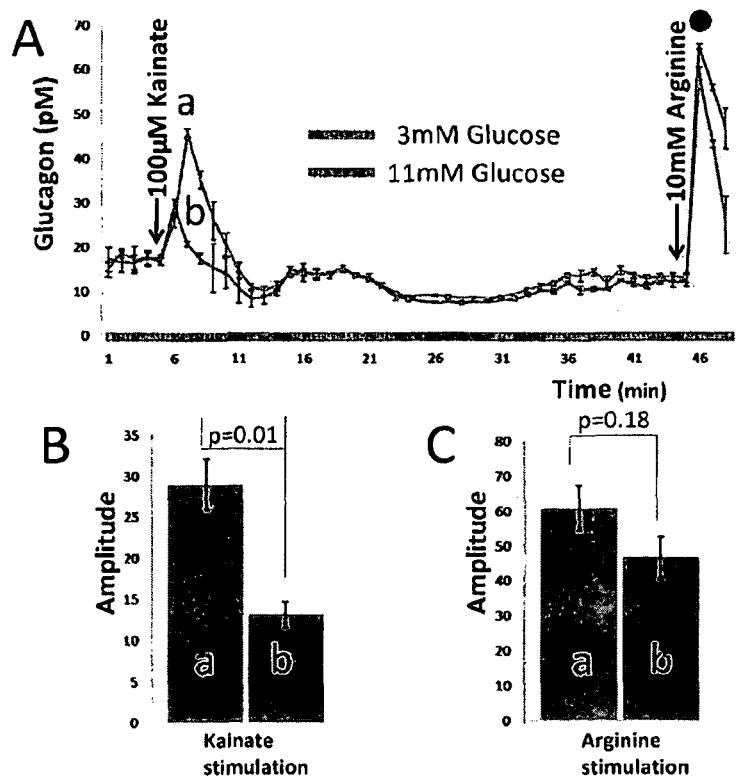
FIG. 9 shows an example of the potentiation of glucagon release by glutamate is reduced in the absence of β cell, a situation that models diabetes. This experiment was performed with mouse islets. Two samples were perifused in parallel ("a" and "b"). In "a" (blue curve and blue bar), but not in "b" (red curve and red bar) the β cells were selectively destroyed with streptozotocin. This absence of β cells generates type 1 diabetes-like condition in vitro. The glucagon release profile in panel "A" was obtained by using this model. In the absence of β cells, kainate is not as effective in potentiating glucagon release as in the presence of the β cells (quantified in panel "B"). Note that the non specific stimulus arginine is not able to differentiate a functionally impaired α cell in the absence of β cells. These data show that a decreased potentiation of glucagon release by kainate can be linked to the lack of glucagon release during hypoglycemia in type 1 diabetes.

We now put forward a model that, at least in part, explains how glucagon release can be effectively regulated in human pancreatic islets (FIG. 7D). When there is a lowering in blood glucose concentration, the negative paracrine influence of β-cells on α-cells decreases ('Switch-off' hypothesis; (fryer et al., 2003; Hope et al., 2004; Zhou et al., 2004). At this stage the glucose concentration is too low to inhibit (Macdonald et al., 2007; MacDonald and Rorsman, 2007) but still high enough to drive (Olsen et al., 2005) partial glucagon release and in parallel glutamate release, creating a positive feedback loop through iGluRs that potentiates α-cell secretory activity. This is in agreement with our results showing that pharmacological blockade of iGluRs exacerbates insulin-induced hypoglycemia and reduces glucagon secretion in vivo.

Accordingly, it is one object to provide methods and assays for detecting and regulating glucagon release and methods of treating hypoglycemia. In some embodiments, these methods can be used for detecting and treating diabetes. However, the methods should also be useful for any insulin induced hypoglycemia.

The term "hypoglycemia" refers to lower than normal levels of blood glucose. The exact ranges for lower than normal levels will depend on the subject because of factors such as age, health, and the subject's average baseline glucose levels. In some embodiments, hypoglycemic glucose blood levels include those below 70 mg/dl or 3.9 mmol/L.

The methods described herein are expected to be particularly useful for the treatment of diabetes mellitus in humans, including both Type 1 and Type 2 diabetes.

The term "subject" is intended to include mammals that are susceptible to affliction with diabetes mellitus, in particular humans, and also includes any mammal in which it may be desirable to treat hypoglycemia.

Some embodiments of the present invention are directed to methods of treating hypoglycemia by administering a compound that directly or indirectly activates an ionotropic glutamate receptor (iGluR) to stimulate glucagon release. In some embodiments, the compound activates the glutamate receptor subunit GluR6.

The compound administered can be, for example, (2S,4R)-4-Methylglutamic acid. The compound can be administered at an effective dose that has been determined by a physician. The dose can range, in some embodiments, from about 5 mg/kg/day to about 200 mg/kg/day depending on the degree of patient's hypoglycemia and other patient specific factors such as age, general health, and the presence of other illnesses.

The compound administered as part of the methods can be an agonist or a partial agonist of the iGluR. In some embodiments, the compound is an agonist or a partial agonist for the glutamate receptor subunit GluR6. An example of an agonist for iGluR is kainate.

Some embodiments of the present invention are directed to assays for testing the regulation of glucagon release. For example, in some embodiments the present invention are directed to an in vitro model in which we destroy selectively the beta cells with, for example, streptozotocin, thus creating a situation that mimics type 1 diabetes. The treated islets are composed mainly of alpha cells. When these alpha cells were stimulated with arginine, an unspecific stimulus for glucagon secretion, their glucagon response was similar to that of alpha cells in control, intact islets. To examine if alpha cells in islets depleted of beta cells had impaired glutamate signaling, we stimulated them with kainate, an agonist for ionotropic glutamate receptors. Alpha cells in islets devoid of beta cells had strongly reduced glucagon responses to kainate. These results indicate that glutamate signaling in alpha cells is specifically downregulated or impaired in islets with the reduced beta cell mass of diabetes.

The following examples are further illustrative of the present invention, but are not to be construed to limit the scope of the present invention.

EXAMPLES

Materials and Methods

Islet Isolation and Culture

Human (n=12, age=48±7 years), monkey (*Macacca fascicularis*; n=15; >4 years of age), and mouse (C57Bl/6; n=15) islets were isolated and cultured as described elsewhere (Cabrera et al., 2006). Mutant mice lacking the metabotropic glutamate receptor mGluR4 (C57Bl/6 background) were purchased from Jackson Laboratories (Bar Harbor, Me.). All experimental protocols using monkeys and mice were approved by the University of Miami Animal Care and Use Committee.

Determination of Cytoplasmic free $Ca^{2+}$

Imaging of $[Ca^{2+}]_i$ was performed as described elsewhere (Cabrera et al., 2006). Islets or dispersed islet cells were immersed in HEPES-buffered solution (mM: 125 NaCl, 5.9 KCl, 2.56 $CaCl_2$, 1 $MgCl_2$, 25 HEPES; 0.1% BSA; pH 7.4). Glucose was added to give a final concentration of 3 mM. Islets or dispersed islet cells were incubated in Fura-2 AM (2 µM; 1 hour) and placed in a closed small-volume imaging chamber (Warner Instruments, Hamden, Conn.). Stimuli were applied with the bathing solution. Islets loaded with Fura-2 were excited alternatively at 340 and 380 nm with a monochromator light source (Cairn. Research Optoscan Monochromator, Cairn Research Ltd, Faversham, UK). Images were acquired with a Hamamatsu camera (Hamamatsu Corp, Japan) attached to a Zeiss Axiovert 200 microscope (Carl Zeiss, Jena, Germany). Changes in the 340/380 fluorescence emission ratio over time were analyzed in individual islets and dispersed cells using Kinetic Imaging AQM Advance software (Kinetic Imaging, N.C.). Peak changes in the fluorescence ratio constituted the response amplitude.

Dynamic Measurements of Glucagon and Insulin Secretion

A high-capacity, automated perifusion system was developed to dynamically measure hormone secretion from pancreatic islets. A low pulsatility peristaltic pump pushed HEPES-buffered solution (mM: 125 NaCl, 5.9 KCl, 2.56 $CaCl_2$, 1 $MgCl_2$, 25 HEPES, and 0.1% BSA; pH 7.4; and a perifusion rate of 100 µL/min) through a column containing 100 pancreatic islets immobilized in Bio-Gel P-4 Gel (Bio-Rad, Hercules, Calif.). Except otherwise stated, glucose concentration was adjusted to 3 mM for all experiments. Stimuli were applied with the perifusion buffer. The perifusate was collected in an automatic fraction collector designed for a 96 well plate format. The columns containing the islets and the perifusion solutions were kept at 37° C., and the perifusate in the collecting plate was kept at <4° C. Perifusates were collected every minute. Hormone release in the perifusate was determined with the human or mouse Endocrine LINCOplex Kit following manufacturer's instructions (Linco research, St. Charles, Mo.).

Real Time Determination of Glucagon Release with Biosensor Cells

HEK293H-CNG cells stably expressing human glucagon receptor (glucagon biosensor cells) from BD Biosciences (San Jose, Calif.) were used to measure glucagon release in real time. Glucagon biosensor cells were grown in Dulbecco's Modified Eagle Medium (DMEM) supplemented with fetal bovine serum (10%) (Invitrogen), Puromycin (10 mg/ml) (BD Biosciences), and G418 sulfate (500 mg/ml) (Mediatech, Va.). Glucagon biosensor cells were loaded with Fura-2 AM (2 µM; 30 minutes at 37° C.). After washing off excess of Fura-2 AM, pancreatic islets were placed on top of the glucagon biosensor cells and mounted in a closed, small-volume imaging chamber (Warner Instruments) to measure $[Ca^{2+}]_i$ as described above. Perifusion of the islets was stopped after addition of the stimulus to allow the islet secretory products to accumulate and then resumed after 10 minutes. The glucagon response profiles obtained with this technique resembled those obtained in perifusion studies, but the biosensor cell assay was more sensitive and showed less variability.

Microfluorometric Determination of Endogenous Glutamate Release

Endogenous glutamate release from pancreatic islets was measured with the Amplex Red Glutamic Acid Assay Kit (Molecular Probes) adapted for microscopic microfluorometric detection (Akagi et al., 2003). In this assay, released glutamate is a substrate in an enzymatic chain reaction that generates the highly fluorescent product resorufin (Molecular Probes, Eugene, Oreg.). L-glutamate is oxidized by glutamate oxidase to produce α-ketoglutarate, $NH_4$, and $H_2O_2$. Hydrogen peroxide reacts with the Amplex Red reagent in a reaction catalyzed by horseradish peroxidase to generate resorufin. Pancreatic islets were allowed to attach to a glass coverslip previously coated with poly-D-lysine. The coverslip was mounted in a closed small-volume imaging chamber (Warner Instruments) and perifused with the HEPES-buffered solution containing the stimuli. Resorufin fluorescence was excited at 510 nm, and the emission recorded at 590 nm using the same imaging system used to measure $[Ca^{2+}]_i$ (see above).

Patch Clamp Electrophysiology

Membrane currents were measured using whole-cell patch clamp recordings of dispersed human islet cells. All recordings were amplified using an EPC10 patch-clamp amplifier and digitized and analyzed using Patchmaster software (Heka Elektronik, Lambrecht, Germany). Pipettes were pulled from borosilicate glass capillaries on a horizontal programmable puller (DMZ Universal Puller, Zeitz-Instrumente, Augsburg, Germany). Pipettes with a resistance of 5-7 MΩ were filled with a pipette solution containing (in mM): 150 NMG (N-methyl-D-Glucamine), 10 EGTA, 1 $MgCl_2$, 2 $CaCl_2$, 5 HEPES and 3 Mg-ATP (pH 7.15). The bath solution contained (in mM): 138 NaCl, 5.6 KCl, 1.2 $MgCl_2$, 2.6 $CaCl_2$, 5 HEPES and 10 TEA (pH7.4). Cells were voltage-clamped at −70 mV. Ligands (e.g. kainate) were applied using the SF-77B Perfusion Fast-Step system (Warner Instruments, Hamden, Conn.), which allows rapid change of solutions bathing a single cell or membrane patch attached to a patch electrode. We did not attempt to identify cell type based on electrophysiological characterization because >75% of the kainate responsive cells in our $[Ca^{2+}]_i$ imaging experiments were glucagon immunoreactive cells. Thus, it is most likely that cells responding to kainate in our electrophysiological experiments were α-cells.

RT-PCR

Total RNA from >90% pure human and monkey islets was isolated using the RNA Easy kit from Qiagen (Valencia, Calif.). cDNA was synthesized from 500 ng of total RNA using the SuperScript™ First-Strand Synthesis System (Invitrogen). cDNA (2 μl) was used without further purification for PCR reaction (35 cycles) with the LightCycler and Roche amplification kit. Primers for human AMPA/Kainate (GluR1-7, Ka1 and KA2) and vesicular glutamate transporters (vGluT1-3) were purchased from Qiagen and used at the concentrations suggested by the vendor.

Single Cell RT-PCR

Human or monkey islets were dispersed into individual cells. Single cells were harvested using glass micropipettes (~20 μm) and placed in centrifuge tubes. mRNA was reverse transcribed using the SuperScript First Strand Synthesis System (Invitrogen). Real time PCR was performed using the TaqMan Fast Universal PCR Master Mix and the 7500 or 7900HT Fast Real-Time PCR Systems (Applied Biosystems). The TaqMan assays were chosen to span an exon junction and therefore did not detect genomic DNA. We first amplified each cDNA with TaqMan probes specific for insulin, glucagon, somatostatin, and pancreatic polypeptide. Cells expressing exclusively one of the pancreatic hormones were used for further PCR to detect the glutamate receptor units GRIA1-4 (AMPA receptor subunits) and GRIK1-5 (kainate receptor subunits), and the metabotropic glutamate receptors 4 and 5 (GRM4 and GRM5).

Immunofluorescence

Immunofluorescence procedures were as described elsewhere (Cabrera et al., 2006). Blocks of human, monkey, or mouse pancreas (0.5 $cm^3$) or isolated islets were fixed in 4% paraformaldehyde (4-6 h) and frozen. Sections (14 μm) were cut on a cryostat. After a rinse with OptiMax Wash Buffer (Biogenex, San Ramon, Calif.), sections were incubated in Universal Blocker Reagent (5-10 minutes; Biogenex), rinsed again in OptiMax Wash Buffer, and incubated in Protein Block (20 minutes, Biogenex). Thereafter, sections were incubated overnight with anti-insulin (1:500, Accurate Chemical & Scientific Corp., NY), anti-glucagon (1:2000; Sigma, St Louis Mo.), anti-somatostatin (1:500; Serotec, N.C.), and anti-pancreatic polypeptide (1:100, Serotec) antibodies. To visualize vesicular glutamate transporters (vGluTs), sections were incubated in anti-vGluT1 (1:20,000; Chemicon), anti-vGluT2 (1:10,000; Chemicon), or anti-vGluT3 (1:20,000; Chemicon) together with antisera against insulin and glucagon. To visualize neuronal elements, isolated human islets were immunostained in rabbit anti-synapsin 1/2 (1:500; Synaptic Systems, Gottingen, Germany), mouse anti-neuron specific enolase (1:500, Chemicon), rabbit anti-neurofilament 200 (1:100, Sigma), or chicken anti-neurofilament H (1:200, Neuromix). Immunostaining was visualized using Alexa conjugated secondary antibodies (1:400; Molecular Probes, Eugene, Oreg.). Cell nuclei were stained with DAPI (Molecular Probes). Slides were mounted with ProLong Anti Fade (Molecular Probes) and cover-slipped. As a negative control we substituted the primary antibody with the serum of the animal used to raise this antibody. No staining was observed under these conditions. Pancreatic sections containing islets were examined for the expression of the different endocrine markers and vGluTs using a Zeiss LSM 510 scanning confocal microscope (Zeiss, Jena, Germany). We chose an optical section of 1 μm for all image acquisitions. All images were digitally acquired and not further processed. Sections were viewed at 20 and 40× magnification. Digital images were compiled using Adobe Photoshop 7.0 (Adobe Systems Inc., San Jose Calif.). Only brightness and contrast were adjusted.

In Vivo Studies

We examined in vivo responses to iGluR agonists by injecting C57BL/6 mice i.p. with either PBS (n=4), monosodium glutamate (30 mg/kg; n=7), or AMPA (15 mg/kg; n=8). To determine whether blocking iGluRs exacerbates insulin-induced hypoglycemia, we injected the AMPA/kainate iGluR antagonist NBQX (Tocris, Ellisville, Mo.) i.p. at 20 mg/kg 30 minutes before mice were treated with insulin to induce hypoglycemia.

Hyperinsulinemic-Hypoglycemic Clamp in Conscious Mice

To provide a standardized hypoglycemic stimulus we further conducted studies using the hyperinsulinemic-hypoglycemic clamp. At least 4 days before the experiments, mice were anesthetized with isoflurane, and an indwelling catheter was inserted in the left jugular vein and externalized through an incision in a skin flap behind the head. Mice were fasted for 4 hours and placed in individual plastic containers for tail cut sampling. Tail blood samples (20 μl) were taken before the start of the experiment for the determination of basal plasma glucagon and insulin secretion. A priming dose of insulin (100 mU/kg) was administered, followed by a constant infusion rate of 20 mU/kg/min (Actrapid, Novo Nordisk). The plasma glucose concentration was determined at 10 min intervals using a One Touch Ultra glucose meter. Glucose (30%) was infused at a variable rate to maintain the plasma glucose concentration at the hypoglycemic levels (~3 mM). At time 50 min, a hyperinsulinemic-hypoglycemic clamp was achieved. Blood glucose levels were kept at the steady state (3 mM) and NBQX was administered as a bolus (10 mg/kg) at time 60 min, followed by infusion (10 mg/kg) until the end of the experiment. A control experiment was performed using saline (0.9% NaCl) following the same protocol used for NBQX. Tail blood samples (20 μl) were taken at several time points: 0, 50, 75 and 90 min for the determination of plasma glucagon and insulin secretion. Animals were euthanized by an over-dose of pentobarbital.

Statistical Analyses

For statistical comparisons described herein a Student's t-test, one-way ANOVA, or repeated measures ANOVA followed by multiple comparisons procedures with the Student-Newman-Keuls method was used.

Example 1

Figure 2:
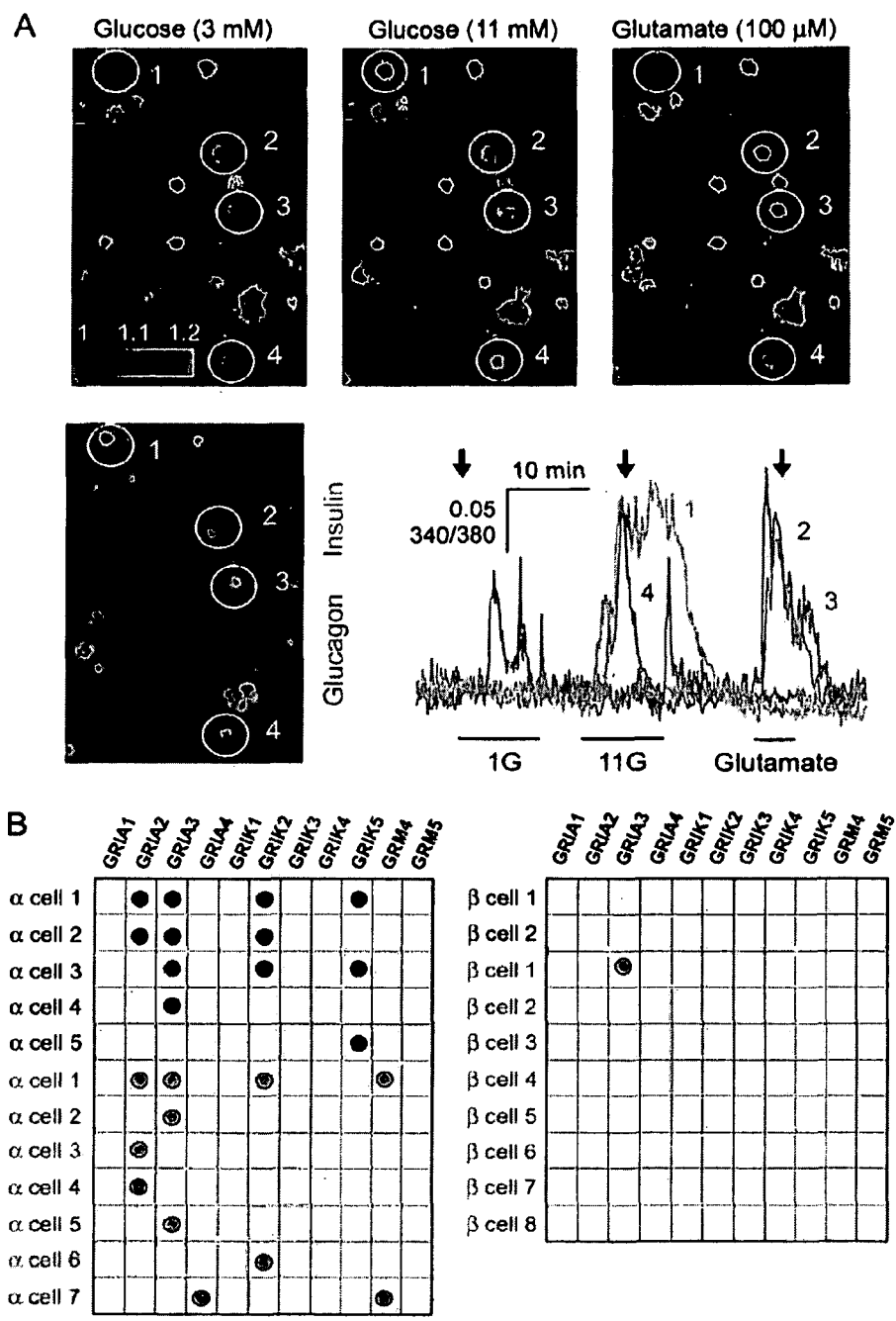
FIG. 2 A-B shows an example of α-cells in human pancreatic islets express functional ionotropic glutamate receptors (iGluRs) of the AMPA/kainate type.

Activation of Ionotropic Glutamate Receptors in Human Islets Induces Glucagon Secretion By performing RT-PCR on isolated human and monkey islets we could detect transcripts for the iGluR subunits GluR1, GluR2, GluR3, and GluR4 of the AMPA receptor type and GluR5, GluR6, GluR7 and KA2 of the kainate receptor type (not shown). These results are in agreement with those published in the Beta Cell Consortium Database (http://www.betacell.org/resources/data/epcondb/). The expression of iGluR subunits in islets was confirmed by immunoblot analysis with antibodies against GluR2/3 (not shown). GluR1 and GluR4 subunits could not be detected. The bands of the correct size disappeared from the immunoblots when the GluR2/3 antibody was pre-adsorbed, but the immunostaining in pancreas sections did not, indicating that the immunofluorescent signal obtained with the GluR2/3 antibodies was not specific. To study cell-specific expression of iGluRs we thus decided to use alternative techniques (see below).

in contrast to previous results in rodent islets (Moriyarna and Hayashi, 2003), we found that functional AMPA/kainate iGluRs were present exclusively in α-cells of human and monkey islets (FIGS. 1, 2). By using the in vitro perifusion technique to detect hormone secretion, we determined that glutamate (1 μM-1 mM) stimulated large, concentration-dependent increases in glucagon release (FIG. 1A, B). Increases in glucagon release could also be elicited by the iGluR agonists kainate (100 μM) and AMPA (100 μM; FIG. 1A, B). CNQX (10 μM) and DNQX (10 μM; not shown), two antagonists for iGluRs of the AMPA/kainate type, inhibited glutamate-induced glucagon release by more than 90% (FIG. 1A, B). Metabotropic receptors have been reported to mediate negative autocrine effect on glucagon secretion in rat islets (Uehara et al., 2004). Using human islets, however, we found that the metabotropic receptor agonists trans-ACPD (100 μM) and ACPT-1 (100 μM), and the metabotropic antagonist CPPG (100 μM) did not affect basal glucagon secretion or glucagon responses to glutamate (FIG. 1C, D).

Neither kainate (100 μM), glutamate (100 μM), nor AMPA (100 μM) stimulated increases in insulin release in human (FIG. 1E) and monkey islets (not shown). These effects of iGluRs agonists were similar at all glucose concentrations tested (1 mM, 3 mM, and 11 mM).

Example 2

Alpha Cells Express Functional iGluRs of the AMPA/Kainate Type

Human and monkey islets as well as dispersed single islet cells loaded with the $Ca^{2+}$ indicator Fura-2 showed increases in cytoplasmic free $Ca^{2+}$ concentration ($[Ca^{2+}]_i$) in response to glutamate (100 μM). $[Ca^{2+}]_i$ responses to glutamate were concentration dependent (FIG. 1F) and could be blocked by CNQX (10 μM) (see below). The range of glutamate concentrations that elicited $[Ca^{2+}]_i$ responses was similar to that reported for neurons in the central nervous system (Hollmann and Heinemann, 1994; Seeburg, 1993). Cells that responded to glutamate also responded to kainate (100 μM) with large increases in $[Ca^{2+}]_i$ (12 out of 12 cells). Cells that responded to glutamate in terms of increases in $[Ca^{2+}]_i$ did not respond to high glucose concentrations (11 mM; n=43 out of 43 cells; FIG. 2A), and cells that responded to high glucose did not respond to glutamate (n=64 out of 64 cells; FIG. 2A). Using immunofluorescence after $[Ca^{2+}]_i$ imaging, we found that most glutamate-responsive cells were glucagon-immunoreactive (n=34 out of 37 cells; n=4 human preparations; FIG. 2A). None of the insulin immunoreactive cells responded to kainate (n=8), but most of the glucagon immunoreactive cells did (7 out of 9). Similar results were obtained with monkey islets (not shown).

Single cell RT-PCR experiments showed that transcripts for the AMPA/kainate genes GRIA2, GRIA3, and GRIK2 (FIG. 2B) could be detected consistently in cells identified as α-cells (positive for glucagon, but not insulin, somatostatin, or pancreatic polypeptide; n=7 human cells, n=5 monkey cells). By contrast, in identified β-cells (positive for insulin only) we could not detect transcripts for AMPA/kainate genes (FIG. 2B). Transcripts for the metabotropic glutamate receptor 4 gene (GRM4) were found in 2 out of 7 human α-cells, but not in monkey α-cells or in β-cells of both species (FIG. 2B). None of the examined cells contained transcripts for the metabotropic glutamate receptor 5 gene (GRM5). These data indicate that human and monkey α-cells, but not β-cells, express functional iGluRs of the AMPA/kainate type.

Example 3

Figure 3:
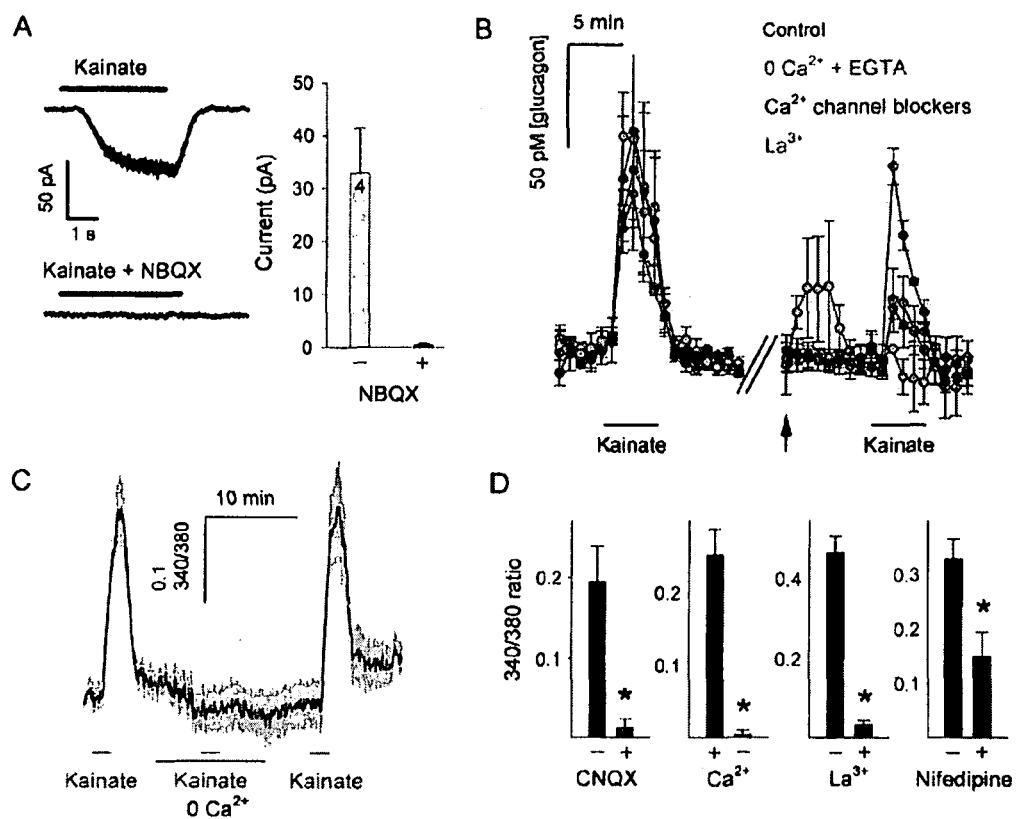
FIG. 3 A-C shows that α-cell responses to kainate require $Ca^{2+}$ influx through voltage-dependent $Ca^{2+}$ channels.

Activation of AMPA/Kainate Receptors Elicits Glucagon Secretion Via $Ca^{2+}$ Influx Through Voltage-Gated $Ca^{2+}$ Channels The inventors examined how activation of AMPA/kainate iGluRs can lead to glucagon secretion. Whole-cell patch clamp recordings on isolated human islet cells showed that application of kainate (100 μM) elicited inward currents that could be blocked by NBQX (10 μM), an AMPA/kainate receptor antagonist (FIG. 3A). $[Ca^{2+}]_i$ responses to kainate were blocked by CNQX (10 μM) and were abolished in the absence of extracellular $Ca^{2+}$ and by $La^{3+}$ (30 μM), a potent blocker of voltage-gated $Ca^{2+}$ channels (FIG. 3C, D). The L-type $Ca^{2+}$ channel blocker nifedipine (10 μM) reduced kainate-induced $[Ca^{2+}]_i$ responses by ~60% (FIG. 3D). We further investigated whether these mechanisms are involved in kainate-induced glucagon secretion. Using perifusion assays to detect hormone secretion, we found that kainate-stimulated glucagon secretion was abolished in the absence of extracellular $Ca^{2+}$ (FIG. 3B). $La^{3+}$ (30 μM) and a combination of selective $Ca^{2+}$ channel inhibitors greatly diminished (>90%) the glucagon response to kainate. These results indicate that kainate elicited glucagon secretion by activating inward currents through AMPA/kainate iGluRs (Hollmann and Heinemann, 1994; Mayer and Armstrong, 2004), which depolarize the α-cell plasma membrane, resulting in $Ca^{2+}$ influx through voltage-gated $Ca^{2+}$ channels and consequently an increase in $[Ca^{2+}]_i$.

Example 4

Primate α-Cells Secrete Glutamate

Figure 4:
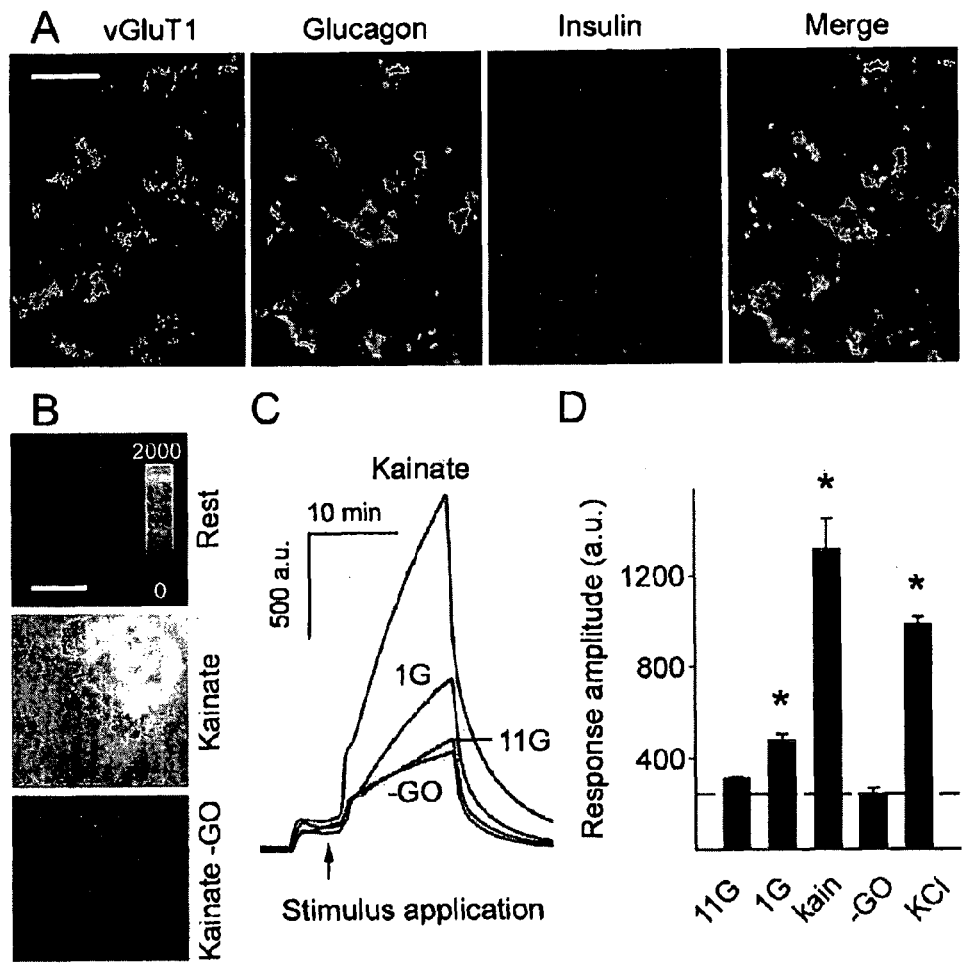
FIG. 4 A-D shows an example of release of glutamate in stimulated primate α-cells.

There are several putative sources of glutamate in islets, e.g. nerve terminals and endocrine cells. We therefore investigated whether glutamate is released from the glucagon-containing α-cells. Cells capable of vesicular release of glutamate express vesicular glutamate transporters [vGluTs; (Fremeau et al., 2004)]. Our RT-PCR results indicate that primate islets express vGluT1 and vGluT2 (not shown). To investigate the localization of vGluTs in primate islets we performed multiple immunostaining on human and monkey pancreatic sections (FIG. 4A). In line with previous studies in rat (Hayashi et al., 2003a; Hayashi et al., 2003b), we found that α-cells, but not insulin-containing β-cells, were immunoreactive for vGluT1 (FIG. 4A). These results indicate that α-cells are a major source of glutamate within the primate islet.

To visualize glutamate release directly, we adapted an enzymatic assay for microfluorometric detection of extracellular glutamate (Akagi et al., 2003) and performed this assay using isolated, cultured islets (FIG. 4B). When the glucose concentration was lowered from 6 mM to 1 mM, fluorescence intensity increased significantly, indicating that glutamate was released (FIG. 4C, D). By contrast, stimulation with high glucose concentrations (11 mM) did not induce glutamate secretion (FIG. 4C, D). When stimulated with kainate (100 μM), a stimulus specific for α-cells (see above), islets strongly released glutamate (FIG. 4B-D). KCl (30 mM) depolarization also elicited large increases in glutamate release (FIG. 4D). Fluorescent signals were small in the absence of the glutamate-sensitive enzyme glutamate oxidase (FIG. 4B-D), indicating that the large increases in fluorescence intensity in this assay depended on the release of glutamate.

To determine whether neuronal elements could contribute to the glutamate signal, we examined isolated islets for the presence of the neuronal markers synapsin, neuron specific enolase, neurofilament 200, or neurofilament H. We found few if any labeled fibers, boutons, or cells (not shown), which is in agreement with a previous study showing that very few nerve terminals survive overnight islet culture (Karlsson et al., 1997). Because we performed our experiments using cultured islets, we conclude that intra-islet glutamate was mainly derived from stimulated primate α-cells.

Example 5

Glutamate Signaling Provides Positive Feedback for Glucagon Secretion

The results disclosed herein show that α-cells express iGluRs and secrete glutamate, suggesting that glutamate is an autocrine signal. We hypothesized that a decrease in the glucose concentration activates a glutamate feedback loop that potentiates glucagon secretion. If so, applying an iGluR antagonist should reduce the glucagon response. Instead of testing this hypothesis with perifusion assays, which may not be sensitive to detect responses to low concentrations of glucose (Hope et al., 2004), we decided to use a more sensitive assay, namely detection of glucagon release by biosensor cells. We placed human islets on a layer of biosensor cells expressing glucagon receptors (Llorente et al., 2006) ($EC_{50}$ for glucagon=30 pM) (FIG. 5A). The biosensor cells express cyclic nucleotide-gated channels, which are activated by elevated intracellular levels of cAMP subsequent to stimulation of the glucagon receptors, resulting in membrane depolarization and $Ca^{2+}$ influx. Glucagon release from islets was monitored in real time by recording $[Ca^{2+}]_i$ responses from the biosensor cells loaded with the $[Ca^{2+}]_i$ indicator Fura-2. In the absence of islets, biosensor cells did not respond to glutamate (100 μM) (FIG. 5B) or a change in glucose concentrations (not shown). When human islets were placed on biosensor cells, the biosensor cells showed large $[Ca^{2+}]_i$ responses to glutamate application (FIG. 5B), indicating that glucagon release was induced. Lowering the glucose concentration from 6 mM to 1 mM also induced glucagon release, as measured by the $[Ca^{2+}]_i$ responses in biosensor cells (FIG. 5C). The glucagon response to decreasing the glucose concentration was inhibited by CNQX (10 μM) (54% reduction; FIG. 5D). Hence, we conclude that activation of iGluRs on α-cells is necessary for prompt glucagon secretion when the glucose concentration decreases.

Example 6 iGluRs on α-Cells Contribute to In Vivo Glucose Homeostasis

Figure 6:
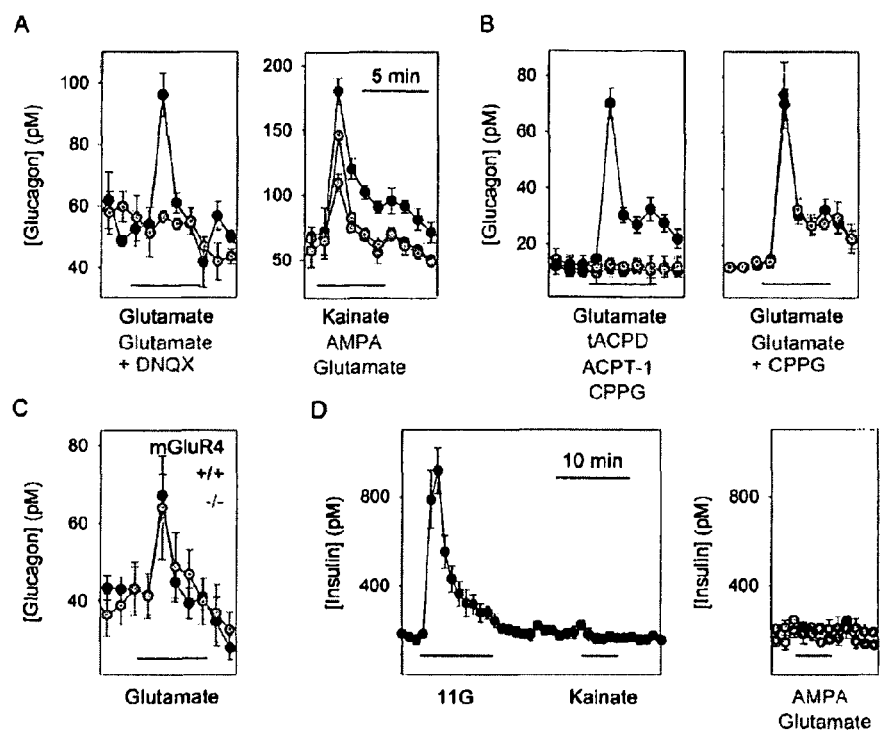
FIG. 6 A-D shows an example of glutamate signaling in mouse islets being similar to that in primate islets.

For example, we have found that activation of AMPA/kainate receptors is among the strongest stimuli for glucagon secretion in vitro. To determine whether activation of iGluRs on α-cells contributes to in vivo glucose homeostasis, we performed experiments in mice. Mouse islets in vitro secreted glucagon, not insulin, in response to AMPA/kainate iGluR activation (FIG. 6A, D). The metabotropic receptor agonists trans-ACPD (100 μM) and ACPT-1 (100 μM) and the metabotropic receptor antagonist CPPG (100 μM) did not affect basal or glutamate-induced glucagon secretion (FIG. 6B). Moreover, glucagon responses to glutamate were undistinguishable in wild type and mGluR4KO mice (FIG. 6C). Therefore, mouse α-cells, but not β-cells, responded to glutamate mainly via activation of iGluRs. These results indicate that glutamate signaling in mouse islets is similar to that in human islets.

To determine if in vivo activation of AMPA/kainate receptors affects glucagon secretion, we injected mice with glutamate and the AMPA receptor specific agonist AMPA. Mice injected with glutamate (30 mg/kg; i.p.) and AMPA (15 mg/kg; i.p.) showed increased plasma glucagon concentrations at 30 minutes after treatment (FIG. 7A). Plasma insulin concentrations were not affected. Concomitantly, these mice had increased glucose levels (FIG. 7A), which should be the result of the increased glucagon secretion. Glutamate and AMPA most likely did not have central effects because glutamate does not penetrate the blood-brain barrier (Beyreuther et al., 2007) and, at the concentrations used, AMPA did not induce convulsions indicative of central nervous penetration (Arnt et al., 1995). Although we cannot rule out effects on peripheral neurons, the collective interpretation of our results strongly suggests that we indeed directly activated AMPA/kainate receptors on α-cells and thereby stimulated glucagon secretion in mice in vivo.

Increased glucagon secretion from α-cells in the endocrine pancreas plays a primary role in glucose counterregulation (Banarer et al., 2002; Rizza et al., 1979). We asked whether α-cells require glutamate positive feedback loops to produce a full glucagon response to a lowering in the glucose concentration. In initial experiments, mice were injected with insulin (1.5 U/kg; i.p.) to induce hypoglycemia. In these mice, systemic treatment with the AMPA/kainate iGluR antagonist NBQX (20 mg/kg, i.p.) increased the insulin-induced drop in glucose plasma levels (not shown). At this concentration, NBQX did not cause sedation, suggesting that the treatment impaired glucose counterregulation without central effects on autonomic functions (Lees, 2000).

To examine whether blocking AMPA/kainate receptors diminishes the counterregulatory response to systemic hypoglycemia we used the hyperinsulinemic-hypoglycemic clamp technique (FIG. 7B). This technique provides a standardized hypoglycemic stimulus where plasma glucose concentrations can be held at a desired level of glycemia (~3 mM in our study). Mice treated systemically with the AMPA/kainate iGluR antagonist NBQX (10 mg/kg; iv; n=7) needed larger infusion rates of glucose to maintain the desired level of glycemia, suggesting that, compared to control, PBS injected mice (n=4), the counterregulatory response was diminished (FIG. 7C). Indeed, we found that glucagon plasma levels were lower in NBQX-treated mice, indicating that activation of iGluRs is needed for efficient glucagon secretion in response to hypoglycemia (FIG. 7B).

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents. Any headings used herein are provided solely for organizational purposes and are not intended to impart any division or meaning to this document, unless specifically indicated.

All documents cited herein, including websites, journal articles or abstracts, published or corresponding U.S. or foreign patent applications, issued or foreign patents, or any other documents, are each entirely incorporated by reference herein, including all data, tables, figures, and text presented in the cited document.

REFERENCES

The following references are each incorporated herein in their entirety:

Akagi, Y., Hashigasako, A., Degenaar, P., Iwabuchi, S., Hasan, Q., Morita, Y., and Tamiya, E. (2003). Enzyme-linked sensitive fluorometric imaging of glutamate release from cerebral neurons of chick embryos. J Biochem (Tokyo) 134, 353-358.

Arnt, J., Sanchez, C., Lenz, S. M., Madsen, U., and Krogsgaard-Larsen, P. (1995). Differentiation of in vivo effects of AMPA and NMDA receptor ligands using drug discrimination methods and convulsant/anticonvulsant activity. Eur J Pharmacol 285, 289-297.

Banarer, S., McGregor, V. P., and Cryer, P. E. (2002). Intraislet hyperinsulinemia prevents the glucagon response to hypoglycemia despite an intact autonomic response. Diabetes 51, 958-965.

Bertrand, G., Gross; R., Puech, R., Loubatieres-Mariani, M. M., and Bockaert, J. (1992). Evidence for a glutamate receptor of the AMPA subtype which mediates insulin release from rat perfused pancreas. British Journal of Pharmacology 106, 354-359.

Bertrand, G., Gross, R., Puech, R., Loubatieres-Mariani, M. M., and Bockaert, J. (1993). Glutamate stimulates glucagon secretion via an excitatory amino acid receptor of the AMPA subtype in rat pancreas. Eur J Pharmacol 237, 45-50.

Bertrand, G., Puech, R., Loubatieres-Mariani, M. M., and Bockaert, J. (1995). Glutamate stimulates insulin secretion and improves glucose tolerance in rats. The American journal of physiology 269, E551-556.

Beyreuther, K., Biesalski, Fernstrom, J. D., Grimm, P., Hammes, W. P., Heinemann, U., Kempski, O., Stehle, P., Steinhart, H., and Walker, R. (2007). Consensus meeting: monosodium glutamate—an update. Eur J Clin Nutr 61, 304-313.

Cabrera, O., Berman, D. M., Kenyon, N. S., Ricordi, C., Berggren, P. O., and Caicedo, A. (2006). The unique cytoarchitecture of human pancreatic islets has implications for islet cell function. Proc Natl Acad Sci USA 103, 2334-2339.

Cryer, P. E., Davis, S. N., and Shamoon, H. (2003). Hypoglycemia in diabetes. Diabetes Care 26, 1902-1912.

Franklin, I., Gromada, J., Gjinovci, A., Theander, S., and Wollheim, C. B. (2005). Beta-cell secretory products activate alpha-cell ATP-dependent potassium channels to inhibit glucagon release. Diabetes 54, 1808-1815.

Fremeau, R. T., Jr., Voglmaier, S., Seal, R. P., and Edwards, R. H. (2004). VGLUTs define subsets of excitatory neurons and suggest novel roles for glutamate. Trends in Neurosciences 27, 98-103.

Gonoi, T., Mizuno, N., Inagaki, N., Kuromi, H., Seino, Y., Miyazaki, J. I., and Seino, S. (1994). Functional neuronal ionotropic glutamate receptors are expressed in the non-neuronal cell line MIN6. Journal of Biological Chemistry 269, 16989-16992.

Gopel, S. O., Kanno, T., Barg, S., Weng, X. G., Gromada, J., and Rorsman, P. (2000). Regulation of glucagon release in mouse-cells by KATP channels and inactivation of TTX-sensitive Na+ channels. J Physiol 528, 509-520.

Gromada, J., Franklin, I., and Wollheim, C. B. (2007). {alpha}-Cells of the Endocrine Pancreas: 35 Years of Research but the Enigma Remains. Endocr Rev 28, 84-116.

Hayashi, M., Morimoto, R., Yamamoto, A., and Moriyama, Y. (2003a). Expression and localization of vesicular glutamate transporters in pancreatic islets, upper gastrointestinal tract, and testis. J Histochem Cytochem 51, 1375-1390.

Hayashi, M., Otsuka, M., Morimoto, R., Hirota, S., Yatsushiro, S., Takeda, J., Yamamoto, A., and Moriyama, Y. (2001). Differentiation-associated Na+-dependent inorganic phosphate cotransporter (DNPI) is a vesicular glutamate transporter in endocrine glutamatergic systems. J Biol Chem 276, 43400-43406.

Hayashi, M., Otsuka, M., Morimoto, R., Muroyama, A., Uehara, S., Yamamoto, A., and Moriyama, Y. (2003b). Vesicular inhibitory amino acid transporter is present in glucagon-containing secretory granules in alphaTC6 cells, mouse clonal alpha-cells, and alpha-cells of islets of Langerhans. Diabetes 52, 2066-2074.

Hayashi, M., Yamada, H., Uehara, S., Morimoto, R., Muroyama, A., Yatsushiro, S., Takeda, J., Yamamoto, A., and Moriyama, Y. (2003c). Secretory granule-mediated co-secretion of L-glutamate and glucagon triggers glutamatergic signal transmission in islets of Langerhans. J Biol Chem 278, 1966-1974.

Hollmann, M., and Heinemann, S. (1994). Cloned glutamate receptors. Annual Review of Neuroscience 17, 31-108.

Hope, K. M., Tran, P. O., Zhou, H., Oseid, E., Leroy, E., and Robertson, R. P. (2004). Regulation of alpha-cell function by the beta-cell in isolated human and rat islets deprived of glucose: the "switch-off" hypothesis. Diabetes 53, 1488-1495.

Inagaki, N., Kuromi, H., Gonoi, T., Okamoto, Y., Ishida, H., Seino, Y., Kaneko, T., Iwanaga, T., and Seino, S. (1995). Expression and role of ionotropic glutamate receptors in pancreatic islet cells. Faseb J 9, 686-691.

Ishihara, H., Maechler, P., Gjinovci, A., Herrera, P. L., and Wollheim, C. B. (2003). Islet beta-cell secretion determines glucagon release from neighbouring alpha-cells. Nat Cell Biol 5, 330-335.

Karlsson, S., Myrsen, U., Nieuwenhuizen, A., Sundler, F., and Ahren, B. (1997). Presynaptic sympathetic mechanism in the insulinostatic effect of epinephrine in mouse pancreatic islets. Am J Physiol 272, R1371-1378.

Kisanuki, K., Kishikawa, H., Araki, E., Shirotani, T., Uehara, M., Isami, S., Ura, S., Jinnouchi, H., Miyamura, N., and Shichiri, M. (1995). Expression of insulin receptor on clonal pancreatic alpha cells and its possible role for insulin-stimulated negative regulation of glucagon secretion. Diabetologia 38, 422-429.

Lees, G. J. (2000). Pharmacology of AMPA/kainate receptor ligands and their therapeutic potential in neurological and psychiatric disorders. Drugs 59, 33-78.

Llorente, I., Lu, J., Titus, S., and Li, X. (2006). BD™ Calcium Assay Kits and BD ACTOne™ Biosensor Technology. HotLines 10, 7-12.

Macdonald, P. E., Marinis, Y. Z., Ramracheya, R., Salehi, A., Ma, X., Johnson, P. R., Cox, R., Eliasson, L., and Rorsman, P. (2007). A KATP Channel-Dependent Pathway within alpha Cells Regulates Glucagon Release from Both Rodent and Human Islets of Langerhans. PLoS Biol 5, e143.

MacDonald, P. E., and Rorsman, P. (2007). The ins and outs of secretion from pancreatic beta-cells: control of single-vesicle exo- and endocytosis. Physiology (Bethesda) 22, 113-121.

Mayer, M. L., and Armstrong, N. (2004). Structure and function of glutamate receptor ion channels. Annu Rev Physiol 66, 161-181.

Molnar, E., Varadi, A., McIlhinney, R. A. J., and Ashcroft, S. J. H. (1995). Identification of functional ionotropic glutamate receptor proteins in pancreatic (beta)-cells and in islets of Langerhans. FEBS Letters 371, 253-257.

Moriyama, Y., and Hayashi, M. (2003). Glutamate-mediated signaling in the islets of Langerhans: a thread entangled. Trends Pharmacol Sci 24, 511-517.

Muroyama, A., Uehara, S., Yatsushiro, S., Echigo, N., Morimoto, R., Morita, M., Hayashi, M., Yamamoto, A., Koh, D. S., and Moriyama, Y. (2004). A novel variant of ionotropic glutamate receptor regulates somatostatin secretion from delta-cells of islets of Langerhans. Diabetes 53, 1743-1753.

Olsen, H. L., Theander, S., Bokvist, K., Buschard, K., Wollheim, C. B., and Gromada, J. (2005). Glucose stimulates glucagon release in single rat alpha-cells by mechanisms that mirror the stimulus-secretion coupling in beta-cells. Endocrinology 146, 4861-4870.

Ravier, M. A., and Rutter, G. A. (2005). Glucose or insulin, but not zinc ions, inhibit glucagon secretion from mouse pancreatic alpha-cells. Diabetes 54, 1789-1797.

Rizza. R. A., Cryer, P. E., and Gerich, J. E. (1979). Role of glucagon, catecholamines, and growth hormone in human glucose counterregulation. Effects of somatostatin and combined alpha- and beta-adrenergic blockade on plasma glucose recovery and glucose flux rates after insulin-induced hypoglycemia. J Clin Invest 64, 62-71.

Rorsman, P., Berggren, P. O., Bokvist, K., Ericson, H., Mohler, H., Ostenson, C. G., and Smith, P. A. (1989). Glucose-inhibition of glucagon secretion involves activation of GABAA-receptor chloride channels. Nature 341, 233-236.

Saper, C. B., and Sawchenko, P. E. (2003). Magic peptides, magic antibodies: guidelines for appropriate controls for immunohistochemistry. The Journal of comparative neurology 465, 161-163.

Seeburg, P. H. (1993). The TiPS/TINS lecture: the molecular biology of mammalian glutamate receptor channels. Trends Pharmacol Sci 14, 297-303.

Storto, M., Capobianco, L., Battaglia, G., Molinaro, G., Gradini, R., Riozzi, B., Di Mambro, A., Mitchell, K. J., Bruno, V., Vairetti, M. P., Rutter, G. A., and Nicoletti, F. (2006). Insulin secretion is controlled by mGlu5 metabotropic glutamate receptors. Molecular Pharmacology 69, 1234-1241.

Uehara, S., Muroyama, A., Echigo, N., Morimoto, R., Otsuka, M., Yatsushiro, S., and Moriyama, Y. (2004). Metabotropic glutamate receptor type 4 is involved in auto-inhibitory cascade for glucagon secretion by alpha-cells of islet of Langerhans. Diabetes 53, 998-1006.

Unger, R. H. (1985). Glucagon physiology and pathophysiology in the light of new advances. Diabetologia 28, 574-578.

Weaver, C. D., Yao, T. L., Powers, A. C., and Verdoorn, T. A. (1996). Differential expression of glutamate receptor subtypes in rat pancreatic islets. J Biol Chem 271, 12977-12984.

Wendt, A., Birnir, B., Buschard, K., Gromada, J., Salehi, A., Sewing, S., Rorsman, P., and Braun, M. (2004). Glucose inhibition of glucagon secretion from rat alpha-cells is mediated by GABA released from neighboring beta-cells. Diabetes 53, 1038-1045.

Zhou, H., Tran, P. O., Yang, S., Zhang, T., LeRoy, E., Oseid, E., and Robertson, R. P. (2004). Regulation of alpha-cell function by the beta-cell during hypoglycemia in Wistar rats: the "switch-off" hypothesis. Diabetes 53, 1482-1487.

We claim:

1. An assay for in vitro screening for modulators useful in treating diabetes comprising:
   (a) administering to islet cells a dose of streptozoticin sufficient to destroy the β cells present;
   (b) administering a test compound to
      (i) a first group of the islet cells administered only the test compound, and
      (ii) a second group of the islet cells administered the test compound and an inhibitor of ionotrophic glutamate receptors (iGluRs); and
   (b) measuring the potentiation of glucagon release in the first and second groups to determine the effect of the test compound, wherein an increase in cytoplasmic calcium mobilization and/or glucagon release in the first group relative to the second group is indicative of a compound that is useful as a modulator of diabetes.

2. The assay of claim 1, wherein the administering the test compound is done under assay condition of between 1 mM and 6 mM glucose.

3. The assay of any claim 1, wherein the first and second group are cultured on glucagon biosensor cells.

4. The assay of any claim 2, wherein the first and second group are cultured on glucagon biosensor cells.

* * * * *